Nov. 26, 1963 | E. S. BOERNER | Plant Pat. 2,321
ROSE PLANT
Filed Oct. 16, 1962
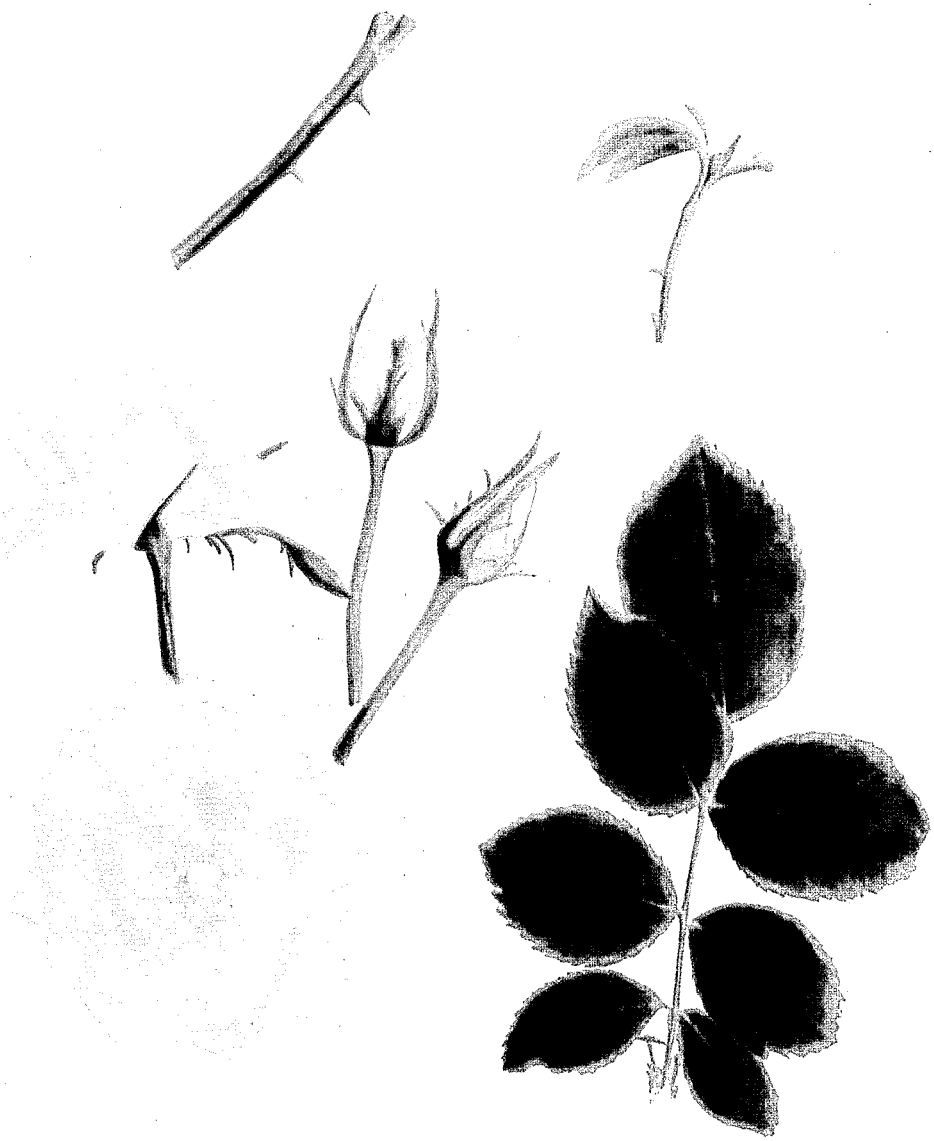
Inventor.
E. S. Boerner
By: Robb & Robb
Attorneys.

United States Patent Office

Plant Pat. 2,321
Patented Nov. 26, 1963

2,321
ROSE PLANT

Eugene S. Boerner, Newark, N.Y., assignor to Jackson & Perkins Company, Newark, N.Y., a corporation of New York Filed Oct. 16, 1962, Ser. No. 231,048
1 Claim. (Cl. Plt.—22)

The present invention relates to a new and distinct varitey of rose plant of the floribunda class, which was originated by me by crossing an unnamed and unpatented yellow-flowered seedling of "Pinocchio" (Plant Patent No. 484) with the variety "Spartan" (Plant Patent No. 1,357).

The primary objective of this breeding was to produce a new rose variety in which there is combined the foliage and bloom characteristics of the parent variety "Spartan," along with the bloom characteristics of the unnamed seedling parent, so that the new variety will be suitable for both indoor and outdoor use. This objective was fully achieved, along with other desirable improvements, as evidenced by the following unique combination of characteristics which are outstanding in the new variety and which distinguish it from its parents, as well as from all other varieties of which I am aware:

(1) Great floriferousness;

(2) A distinctive, attractive and clean Grenadine Red general color tonality of the flowers which is different from the flower color of any other floribunda rose variety known or available in the greenhouse cut flower trade;

(3) Long-lasting qualities of the flowers as cut flowers; and (4) A habit of rapidly repeating buds and blooms after cutting.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
- *Seed parent.*—An unnamed yellow-flowered seedling of "Pinocchio."
- *Pollen parent.*—"Spartan."

Classification:
- *Botanic.*—Floribunda.
- *Commercial.*—Floribunda.

*Flower*

(Observations made from specimens grown in a greenhouse at Newark, New York, in the early morning during the latter part of the month of July.)

Blooming habit: Recurrent—continuous; very floriferous.

Bud:
- *Size.*—Medium.
- *Form.*—Ovoid; is not affected by wet or hot weather.
- *Color.*—When sepals first divide—Rose Red, Plate 12. When petals begin to unfurl—Scarlet, Plate 1. When half-blown: inside of petals—Grenadine, Plate 2, with lower half of petals lightly overcast with Jasper Red, Plate 13; reverse of petals—Strawberry Pink, Plate 1, very lightly overcast with Orange Pink, Plate 2.

- *Sepals.*—Branched; curl back when petals begin to unfurl. Color: inside—Olivine, Plate 32; outside—Light Bice Green, Plate 17.
- *Calyx.*—Color—Biscay Green, Plate 17. Shape—funnel. Size—small. Aspect—smooth. Odor when rubbed—none.
- *Peduncle.* — Length — medium. Aspect—prickly. Strength—erect; slender. Color—Lettuce Green, Plate 5.
- *Opening.*—Opens up well; is not affected by adverse weather conditions.

Bloom:
- *Size.*—Medium. Average size when fully expanded—3 inches.
- *Borne.*—Both singly and several together.
- *Stems.*—Medium length; strong.
- *Form (when first open).*—Cupped. Permanence—retains its form to the end, but outer petals curl back.
- *Petalage.*—Double (full but open center). Number of petals under normal conditions—25.
- *Color.*—Clean. Center of flower—Scarlet, Plate 1. Outer petals—Grenadine Pink, Plate 2, very lightly overcast with Grenadine Red, Plate 2. Base of petals (aiglet)—Lemon Yellow, Plate 4. Inside of petals—Grenadine Red, Plate 2. Reverse of petals—Orange Pink, Plate 2, very lightly overcast with Strawberry Pink, Plate 1. General tonality from a distance—Grenadine Red, Plate 2.
- *Discoloration.*—General tonality at end of first day—Grenadine Pink, Plate 2, lightly overcase with Scarlet, Plate 1. Second day—Grenadine Pink, Plate 2, lightly overcast with Scarlet, Plate 1. Third day—Grenadine Pink, Plate 2, very lightly overcast with Scarlet, Plate 1.

Petals:
- *Texture.*—Thick; is not affected by wet or hot weather.
- *Appearance.*—Inside—satiny. Outside—shiny.
- *Form.*—Oval.
- *Arrangement.* — Imbricated (regularly arranged shingle-like).
- *Petaloids in center.*—Few; small.
- *Persistence.*—Drop off cleanly.
- *Fragrance.*—Moderate. Nature—tea (average hybrid tea scent).
- *Lasting quality.*—On the plant—very long. As cut flower—very long.

*Genital Organs*

Stamens, anthers: Medium size; many; regularly arranged around styles. Color—Apricot Yellow, Plate 4.

Stamens, filaments (threads): Medium length. Color—Pinard Yellow, Plate 4.

Pollen: Color—Maize Yellow, Plate 4.

Styles: Bunched; uneven length; medium length; thin,

Stigmas: Color—Martius Yellow, Plate 4.

Ovaries: All enclosed in calyx.

Hips: None.

Seeds: None.

Form: Bush.

Growth: Vigorous upright.

Foliage: Compound of 5–7 leaflets.
- *Size.*—Medium.
- *Quantity.*—Normal.
- *Color.*—New foliage: upper side—Absinthe Green, Plate 31, lightly overcase with Eugenia Red, Plate 13; under side—Acajou Red, Plate 13. Old foliage: upper side—Forest Green, Plate 17; under side—Light Bice Green, Plate 17, lightly overcast with Acajou Red, Plate 13.

*Shape.*—Oval pointed.
*Texture.*—Upper side—glossy. Under side—smooth.
*Ribs and veins.*—Ordinary.
*Edge.*—Serrated (saw-toothed).
*Serration.*—Both double and single; sharp.
*Leaf stem.*—Color—Rinnemann's Green, Plate 18. Under side—prickly.
*Stipules.*—Short- bearded.

Wood:

*New wood.*—Color—Lettuce Green, Plate 5. Bark—smooth.
*Old wood.*—Color—Cress Green, Plate 31. Bark—smooth.

Thorns:

*Thorns.*—Quantity: on main stalks from base—ordinary; on laterals from stalk—ordinary. Form—narrow base; medium length; straight. Color (when young)—Eugenia Red, Plate 13. Position—irregular.
*Prickles.*—Quantity: on main stalks—none; on laterals none.
*Short needles.*—Quantity: on main stalks—none; on laterals—none.

I claim:

A new and distinct variety of rose plant of the floribunda class, substantially as herein shown and described, characterized particularly as to novelty by the unique combination of a very floriferous habit, a distinctive, attractive and clean Grenadine Red general color tonality of the flowers and their suitability for both indoor and outdoor production, long-lasting qualities of the flowers, and a habit of rapidly repeating buds and blooms after cutting.

No references cited.